United States Patent [19]

Choudhury et al.

[11] Patent Number: 6,110,387

[45] Date of Patent: Aug. 29, 2000

[54] SULFAMATE STABILIZATION OF A BROMINE BIOCIDE IN WATER

[75] Inventors: Pranab Choudhury; Robert L. Davis; Michael J. Sanders; David N. Roark, all of Baton Rouge, La.

[73] Assignee: Albemarle Corporation, Richmond, Va.

[21] Appl. No.: 09/296,499

[22] Filed: Apr. 22, 1999

[51] Int. Cl.[7] ....................................................... C02F 1/76
[52] U.S. Cl. ......................... 210/752; 210/754; 210/758; 422/317
[58] Field of Search .................................. 210/752, 754, 210/758; 422/37

[56] References Cited

U.S. PATENT DOCUMENTS

| | | | |
|---|---|---|---|
| 3,170,883 | 2/1965 | Owen et al. | 252/187 |
| 3,558,503 | 1/1971 | Goodenough et al. | 252/187 |
| 3,749,672 | 7/1973 | Golton et al. | 252/95 |
| 3,767,586 | 10/1973 | Rutkiewic | 252/187 H |
| 4,451,376 | 5/1984 | Sharp | 210/701 |
| 4,642,194 | 2/1987 | Johnson | 210/699 |
| 4,711,724 | 12/1987 | Johnson | 210/699 |
| 5,527,547 | 6/1996 | Hight et al. | 424/661 |
| 5,683,654 | 11/1997 | Dallmier et al. | 422/14 |
| 5,942,126 | 8/1999 | Dallmier et al. | 210/756 |
| 6,007,726 | 12/1999 | Yang et al. | 210/752 |

*Primary Examiner*—David A. Simmons
*Assistant Examiner*—Betsey J. Morrison
*Attorney, Agent, or Firm*—E. E. Spielman, Jr.

[57] ABSTRACT

This invention describes a method for stabilizing bromine biocides in water. A water-soluble bromide salt and a sulfamate source are added to a body of water, and then an oxidant is added to the body of water to form the biocidal bromine species.

14 Claims, No Drawings

SULFAMATE STABILIZATION OF A BROMINE BIOCIDE IN WATER

TECHNICAL FIELD

This invention relates to the stabilization of a bromine biocide in water using sulfamate ions.

BACKGROUND

Bodies of water are commonly sanitized with either a chlorine or bromine biocide. Chlorine biocides are irritating to human mucous membranes and tend to have a strong odor, while bromine biocides are not so irritating, and usually have less odor. Further, bromine biocides are known to be more effective in water than are chlorine biocides. While this suggests that bromine biocides would be favored over chlorine biocides, it is also known that bromine biocides, unlike chlorine biocides, are unstable when exposed to ultraviolet light, making bromine biocides particularly unsuitable for certain applications, such as swimming pools. In order to utilize bromine biocides, an effective method for their stabilization is needed. Introducing to the body of water a reagent which stabilizes the bromine biocide would be an appropriate way to gain the advantages of a bromine biocide. In addition to effectively stabilizing bromine even under exposure to ultraviolet light, the stabilizer must itself be nonhazardous and nonirritating to humans. Moreover, it would be of considerable advantage if the stabilization could be achieved by use of a minimum number of chemical agents, and if the biocidal activity in the water could be accomplished with as little change as possible in routine maintenance operations.

THE INVENTION

This invention provides a facile way to sanitize a body of water utilizing a bromine biocide. The bromine biocide gains stability via use of sulfamate ions as a stabilization reagent. This invention provides for sanitizing new or refilled bodies of water with stabilized bromine, converting chlorine-sanitized bodies of water to stabilized bromine sanitization, and the continuing sanitization of both types of body of water with stabilized bromine biocide. The chemicals described in this invention are inexpensive, are neither hazardous nor irritating to humans at the recommended concentrations, and further are not detrimental to the mechanical components with which the body of water comes into contact.

An embodiment of this invention is a method for sanitizing a body of water at ambient temperature which comprises introducing into the body of water a sulfamate source and a water-soluble bromide salt, followed by periodically introducing enough oxidant to maintain an available bromine concentration in the range of from about 2 ppm to about 6 ppm in the body of water. The sulfamate source may be sulfamic acid or a water-soluble sulfamate salt, and sufficient sulfamate source is added such that a concentration in the range of from about 0.25 millimoles per liter to about 2 millimoles per liter is achieved. Enough water-soluble bromide salt is added to achieve a concentration in the range of from about 0.34 millimoles per liter to about 6.8 millimoles per liter.

Further embodiments and features of this invention will be apparent from the ensuing description and appended claims.

Sulfamic acid or a water soluble sulfamate salt, such as an alkali metal sulfamate or an alkaline earth sulfamate may be the sulfamate source. Examples of water-soluble sulfamate salts include, but are not limited to, potassium sulfamate and magnesium sulfamate; highly preferred as the sulfamate source is sulfamic acid. Sufficient sulfamate source should be added to the body of water to achieve a concentration of sulfamate ions in the range of from about 0.25 millimoles per liter to about 2 millimoles per liter; more preferred is a sulfamate ion concentration in the range of from about 0.36 millimoles per liter to about 1.5 millimoles per liter.

The bromide ion source is a water-soluble bromide salt. Examples of water-soluble bromide salts that may be used include sodium bromide, potassium bromide, calcium bromide, zinc bromide, ammonium bromide, and the like. Preferably, the water-soluble bromide salt is an alkali metal bromide or an alkaline earth bromide. Alkali metal bromides are more preferred; highly preferred as the water-soluble bromide salt is sodium bromide. Enough water-soluble bromide salt should be added to the body of water to yield a bromide ion concentration in the range of from about 0.34 millimoles per liter to about 6.8 millimoles per liter; a more preferred bromide ion concentration is in the range of from about 0.38 millimoles per liter to about 2.9 millimoles per liter.

Preferably, the sulfamate source and the water-soluble bromide salt are introduced to the body of water in amounts such that mole ratio of added bromide ion to added sulfamate ion is in the range of from about 0.5:1 to about 5:1. A more preferred mole ratio of added bromide ion to added sulfamate ion is in the range of from about 0.75:1 to about 4:1.

Generally, the choice of oxidant does not affect the biocidal activity of the oxidized bromine specie(s). Solid oxidants are preferred; these oxidants include oxone® (potassium peroxymonosulfate) and various hypochlorite sources. Oxidants which are hypochlorite sources are a preferred type of oxidant; thus, more preferred oxidants are solid hypochlorite sources. Examples of oxidants which are solid hypochlorite sources include trichloroisocyanuric acid, sodium dichloroisocyanurate, and calcium hypochlorite. Highly preferred oxidants are calcium hypochlorite and trichloroisocyanuric acid, because they dissolve quickly and easily in water. More highly preferred is trichloroisocyanuric acid because it tends to need to be replenished less frequently than calcium hypochlorite. Chlorine, though not a preferred oxidant, may be used in the practice of this invention.

The sulfamate source and the water-soluble bromide salt may be added to the body of water in any order, as long as both are present in the body of water prior to the addition of the oxidant. The sulfamate source and the water-soluble bromide salt may each independently be added to the body of water as a solid or may be predissolved in a separate vessel and then added to the body of water, so long as the amount of each component added should yield a concentration in the body of water as specified above. The sulfamate source and the water-soluble bromide salt may be combined, either in solid form or in solution, prior to their addition to the body of water. Both the sulfamate source and the water-soluble bromide salt may be added, independently or together, in either solid form or in solution, directly to the body of water, to a sidestream of the body of water, or through an automatic feeder.

After the sulfamate source and the water-soluble bromide salt have been added, the oxidant is added to the body of water. The oxidant may be introduced to the body of water as a solid, or it may be predissolved in a separate vessel and then added to the body of water. The oxidant may be added, in either solid form or in solution, to the body of water through an automatic feeder, to a sidestream of the body of water, or directly to the body of water itself. The amount of oxidant added should be such that from about 2 ppm to about 6 ppm of available bromine is present, as ascertained with a bromine test kit. When the available bromine concentration is below about 2 ppm, all that is needed is to add more oxidant, as is normally done in the maintenance of a body of water that has chlorine-based sanitization.

In the course of this invention, the oxidant oxidizes at least a portion of the bromide ions to their biocidally active form(s); at least a portion of the biocidal specie(s) is stabilized by the sulfamate ions. When the biocidal specie(s) is/are consumed, bromide ions result, necessitating the introduction of additional oxidant to the body of water to regenerate biocidal bromine specie(s). The nature of the bromine biocide(s) and the sulfamate stabilized bromine biocidal specie(s) are not known with certainty.

The following examples are presented for purposes of illustration, and are not intended to impose limitations on the scope of this invention.

EXAMPLE 1

Four runs, each in a separate 12,000 gallon swimming pool, were conducted simultaneously during a one-month period. Enough solid NaBr to attain a concentration of $4.85 \times 10^{-4}$M was added directly to the water of each swimming pool; each swimming pool was tested with a different oxidant. Every evening, the same amount of the appropriate oxidant (170 g trichloroisocyanuric acid, 1.5 pounds of oxone, 170 g $Ca(OCl)_2$, or 227 g sodium dichloroisocyanurate) was added in solid form to each pool. Enough solid sulfamic acid to achieve a concentration of $5.15 \times 10^{-4}$M was then added to the water of each of the four pools. Available bromine readings were taken at approximately the same hour the next morning and the same afternoon (prior to the daily addition of oxidant), using a bromine (DPD) test kit. One set of readings was taken before the stabilizer was added to the pools. The results are summarized in Table 1; the numbers reported in Table 1 are the percentage of available bromine remaining in the pool at the time of the afternoon reading.

EXAMPLE 2

The procedure of Example 1 was followed, except as described herein. Each swimming pool had enough solid NaBr to attain a concentration of $9.71 \times 10^{-4}$M added directly to the water. Both the NaBr and the sulfamic acid were present in all of the swimming pools except Pool 3 prior to the addition of any oxidant; thus, only Pool 3 had readings in the absence of stabilizer. The results are summarized in Table 2; the numbers reported in Table 2 are the percentage of available bromine remaining in the pool at the time of the afternoon reading.

EXAMPLE 3

The procedure of Example 2 was followed, except as described herein. Pools 1 and 2 had enough solid NaBr to attain a concentration of $9.71 \times 10^{-4}$M added directly to the water, while Pools 3 and 4 had enough solid NaBr to attain a concentration of $1.45 \times 10^{-3}$M added directly to the water. Also, Pools 1 and 2 were tested with different forms of the same oxidant, while Pools 3 and 4 were tested with different oxidants. The results are summarized in Table 3; the numbers reported in Table 3 are the percentage of available bromine remaining in the pool at the time of the afternoon reading.

COMPARATIVE EXAMPLE

Four runs, each in a separate 12,000 gallon swimming pool, were conducted simultaneously during a period of several hours. Enough solid NaBr to attain a concentration of $1.21 \times 10^{-3}$M was added directly to the water of Pools 1 and 3; enough solid NaBr to attain a concentration of $1.45 \times 10^{-3}$M was added directly to the water of Pools 2 and 4. Enough solid 5,5-dimethylhydantoin (a well-known bromine stabilizing agent) to achieve a concentration of $1.95 \times 10^{-4}$M was then added to the water of Pools 1 and 3; enough solid 5,5-dimethylhydantoin to achieve a concentration of $3.90 \times 10^{-4}$M was then added to the water of Pool 2. Enough solid sulfamic acid to achieve a concentration of $5.15 \times 10^{-4}$M was then added to the water of Pool 4. All four pools were tested with the same oxidant, $Ca(OCl)_2$; 0.25 pounds of $Ca(OCl)_2$ was added in solid form to each pool the evening prior to the run. Starting the next morning, the available bromine was measured every 1.5 hours, using a bromine (DPD) test kit; the data are summarized in Table 4. The numbers in Table 4 are the available bromine measurements in parts per million; clearly, sulfamic acid is a better bromine stabilization agent than is 5,5-dimethylhydantion.

TABLE 1

| | | Day: | | | | | | | | | | | | | | | |
|---|---|---|---|---|---|---|---|---|---|---|---|---|---|---|---|---|---|
| Pool | oxidant | 0** | 2 | 5 | 6 | 7 | 8 | 9 | 12 | 13 | 14 | 15 | 16 | 19 | 20 | 21 | 22 | 23 |
| 1 | Cl$_3$isocya* | 15 | 40 | 48 | 58 | 44 | 49 | 50 | 43 | 46 | 35 | 43 | 48 | 49 | 72 | 52 | 53 | 47 |
| 2 | oxone | 17 | 40 | 46 | 58 | 50 | 47 | 47 | 40 | 48 | 35 | 44 | 48 | 49 | 79 | 56 | 62 | 50 |
| 3 | Ca(OCl)$_2$ | 10 | 53 | 73 | 63 | 64 | 66 | 58 | 58 | 71 | 57 | 56 | 74 | 57 | 69 | 63 | — | 41 |
| 4 | NaCl$_2$isocy* | — | 42 | 63 | 65 | 65 | 58 | 59 | 56 | 54 | 47 | 50 | 58 | 51 | 73 | 52 | 59 | 50 |

*Cl$_3$isocya = trichloroisocyanuric acid; NaCl$_2$isocy = sodium dichloroisocyanurate
**no stabilizer present in pools

TABLE 2

| Pool | oxidant | Day: 1 | 2 | 3 | 4 | 7 | 8 | 9 | 10 | 13 | 16 | 17 | 18 | 19 | 20 | 23 | 24 | 25 | 26 | 27 | 30 | 31 | 32 | 33 | 34 |
|---|---|---|---|---|---|---|---|---|---|---|---|---|---|---|---|---|---|---|---|---|---|---|---|---|---|
| 1 | $Cl_3$isocya* | 44 | 48 | 50 | 51 | 48 | 50 | 52 | 52 | 50 | 68 | 58 | 55 | 60 | 60 | 56 | 67 | 78 | 72 | 67 | 62 | 52 | 72 | 62 | 65 |
| 2 | oxone | 57 | 54 | 57 | 51 | 55 | 61 | 64 | 63 | 62 | 78 | 58 | 62 | 65 | 65 | 66 | 70 | 88 | 71 | 73 | 76 | 41 | 63 | 76 | 73 |
| 3 | $Ca(OCl)_2$ | — | — | — | — | 13** | 61 | 67 | 68 | 56 | 79 | 78 | 69 | 75 | 76 | 74 | 81 | 94 | 83 | 81 | 73 | 75 | 81 | 77 | 77 |
| 4 | $NaCl_2$isocy* | 44 | 41 | 38 | 47 | 49 | 47 | 49 | 50 | 46 | 65 | 44 | 43 | 50 | 53 | 53 | 59 | 74 | 66 | 53 | 54 | 65 | 62 | 56 | 58 |

*$Cl_3$isocya = trichloroisocyanuric acid; $NaCl_2$isocy = sodium dichloroisocyanurate
**no stabilizer present in pools

TABLE 3

| Pool | oxidant | [Br⁻] | Day: 1 | 2 | 3 | 4 | 8 | 9 | 10 | 11 | 14 | 15 | 16 | 17 | 21 | 22 | 23 |
|---|---|---|---|---|---|---|---|---|---|---|---|---|---|---|---|---|---|
| 1 | $Cl_3$isocya*, tablet | $9.71 \times 10^{-4}$M | 71 | 83 | 76 | 92 | 79 | 96 | 71 | 72 | 88 | 100 | 92 | 92 | 86 | 86 | 82 |
| 2 | $Cl_3$isocya*, granular | $9.71 \times 10^{-4}$M | — | — | — | 90 | 82 | 98 | 92 | 69 | 72 | 96 | 89 | 81 | 74 | 68 | 71 |
| 3 | $Ca(OCl)_2$ | $1.45 \times 10^{-3}$M | 85 | 90 | 80 | 89 | 88 | 95 | 86 | 88 | 86 | 97 | 96 | 86 | 88 | 88 | 95 |
| 4 | $Cl_3$isocya*, granular | $1.45 \times 10^{-3}$M | 68 | 67 | 52 | 79 | 64 | 84 | 83 | 60 | 71 | 96 | 92 | 76 | 70 | 60 | 68 |

*$Cl_3$isocya = trichloroisocyanuric acid

TABLE 4

| Pool | stabilizer | [stabilizer] | [Br⁻] | Time: 0 | 1.5 hrs. | 3 hrs. | 4.5 hrs. | 6.5 hrs. |
|---|---|---|---|---|---|---|---|---|
| 1 | DMH* | $1.95 \times 10^{-4}$M | $1.21 \times 10^{-3}$M | 2.2 | 1.4 | 0.6 | 0.4 | — |
| 2 | DMH* | $3.90 \times 10^{-4}$M | $1.45 \times 10^{-3}$M | 1.3 | 0.4 | 0.3 | 0.2 | — |
| 3 | DMH* | $1.95 \times 10^{-4}$M | $1.21 \times 10^{-3}$M | 2.3 | 1.4 | 0.7 | 0.3 | — |
| 4 | sulfamic acid | $5.15 \times 10^{-4}$M | $1.45 \times 10^{-3}$M | 6.0 | 5.1 | 4.0 | 3.2 | 2.6 |

*5,5-dimethylhydantoin

It may be observed that progressively more stabilization of the bromine is occurring as one compares Examples 1, 2, and 3. One possible explanation for this is that each set of test runs was performed during a different month of the year, with an accordingly different amount of ultraviolet radiation. Example 1 was conducted during September; Example 2 was conducted during October; and Example 3 was conducted during November.

While all of the above examples concern swimming pools, it should be apparent that this invention applies to other bodies of water in need of sanitization that are exposed to ultraviolet light.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises," "is," etc.), the reference is to the substance, component or ingredient as it existed at the time just before it was first contacted, blended or mixed with one or more other substances, components and/or ingredients in accordance with the present disclosure. Whatever transformations, if any, that occur in situ as a reaction is conducted is what the claim is intended to cover. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for sanitizing a body of water at ambient temperature which comprises introducing into said body of water
    (i) sufficient sulfamate source, from sulfamic acid or a water-soluble sulfamate salt, to achieve a concentration in the range of from about 0.25 millimoles per liter to about 2 millimoles per liter, and (ii) sufficient water-soluble bromide salt to achieve a concentration in the range of from about 0.34 millimoles per liter to about 6.8 millimoles per liter, followed by periodically introducing enough oxidant to maintain an available bromine concentration in the range of from about 2 ppm to about 6 ppm in said body of water.

2. A process according to claim 1 wherein said sulfamate source is sulfamic acid.

3. A process according to claim 1 wherein the amount of sulfamate source is such that a concentration in the range of from about 0.36 millimoles per liter to about 1.5 millimoles per liter is achieved.

4. A process according to claim 1 wherein said water-soluble bromide salt is sodium bromide, potassium bromide, calcium bromide, zinc bromide, or ammonium bromide.

5. A process according to claim 4 wherein said water-soluble bromide salt is sodium bromide.

6. A process according to claim 1 wherein the amount of water-soluble bromide salt is such that a concentration in the range of from about 0.38 millimoles per liter to about 2.9 millimoles per liter is achieved.

7. A process according to claim 1 wherein the mole ratio of water-soluble bromide salt to sulfamate source is in the range of from about 0.5:1 to about 5:1.

8. A process according to claim 1 wherein said oxidant is calcium hypochlorite, trichloroisocyanuric acid, sodium dichloroisocyanurate, chlorine, or oxone®.

9. A process according to claim 8 wherein said oxidant is trichloroisocyanuric acid.

10. A process according to claim 1 wherein said water-soluble bromide salt is sodium bromide, potassium bromide, calcium bromide, zinc bromide, or ammonium bromide, and wherein said oxidant is calcium hypochlorite, trichloroisocyanuric acid, sodium dichloroisocyanurate, chlorine, or oxone®.

11. A process according to claim 10 wherein the water-soluble bromide salt is sodium bromide, and wherein the oxidant is trichloroisocyanuric acid.

12. A process according to claim 11 wherein the sulfamate source is sulfamic acid.

13. A process according to claim 10 wherein the mole ratio of water-soluble bromide salt to sulfamate source is in the range of from about 0.5:1 to about 5:1.

14. A process according to claim 10 wherein the amount of sulfamate source is such that a concentration in the range of from about 0.36 millimoles per liter to about 1.5 millimoles per liter is achieved, and wherein the amount of water-soluble bromide salt is such that a concentration in the range of from about 0.38 millimoles per liter to about 2.9 millimoles per liter is achieved.

* * * * *